(12) United States Patent
Chin et al.

(10) Patent No.: US 7,871,426 B2
(45) Date of Patent: Jan. 18, 2011

(54) SPINOUS PROCESS FIXATION DEVICE

(75) Inventors: Kingsley Richard Chin, Philadelphia, PA (US); Daniel R. Baker, Seattle, CA (US); Daniel F. Justin, Logan, UT (US)

(73) Assignee: Spinefrontier, LLS, Philadelphia, PA (US)

( * ) Notice: Subject to any disclaimer, the term of this patent is extended or adjusted under 35 U.S.C. 154(b) by 327 days.

(21) Appl. No.: 11/678,879

(22) Filed: Feb. 26, 2007

(65) Prior Publication Data

US 2007/0270840 A1    Nov. 22, 2007

Related U.S. Application Data

(63) Continuation-in-part of application No. 11/609,418, filed on Dec. 12, 2006.

(60) Provisional application No. 60/784,557, filed on Mar. 21, 2006.

(51) Int. Cl.
*A61B 17/70* (2006.01)
(52) U.S. Cl. .................................................. 606/248
(58) Field of Classification Search ............... 606/75, 606/246–251, 253, 277–279, 300, 324; 623/16.11, 623/17.11, 17.16; 403/52, 64, 65, 68, 71, 403/78, 83, 217, 373
See application file for complete search history.

(56) References Cited

U.S. PATENT DOCUMENTS

| | | | |
|---|---|---|---|
| 5,836,948 A * | 11/1998 | Zucherman et al. | 606/249 |
| 2003/0040746 A1* | 2/2003 | Mitchell et al. | 606/61 |
| 2006/0015181 A1 | 1/2006 | Elberg | |
| 2006/0247640 A1 | 11/2006 | Blackwell et al. | |

* cited by examiner

*Primary Examiner*—Eduardo C Robert
*Assistant Examiner*—David Comstock
(74) *Attorney, Agent, or Firm*—AKC Patents LLC; Aliki K. Collins

(57) ABSTRACT

An implantable spinous process stabilization assembly includes a body, a bent arm and a straight arm. The body includes first and second crosspieces arranged parallel to each other, a first plate extending in a direction at right angle to first ends of the first and second crosspieces, first and second rings extending from second ends of the first and second crosspieces, respectively and a second plate extending from a base of the first and second rings, at right angle to the first and second crosspieces and in an opposite direction to the first plate's direction. The bent arm and the straight arm are configured to pivot around an axis perpendicular to the first and second rings and to set first and second pivot angles with the first and second plates, respectively, thereby defining first and second spaces configured to receive and lock onto first and second spinous processes, respectively.

32 Claims, 12 Drawing Sheets

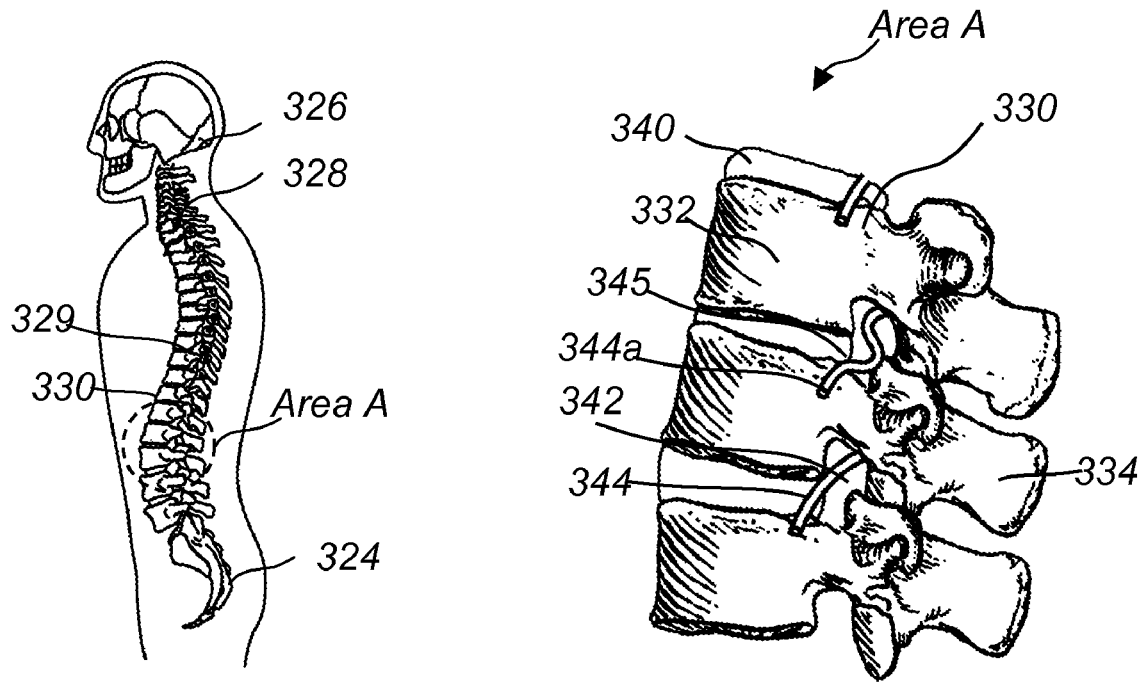
FIG. 12A
FIG. 12B
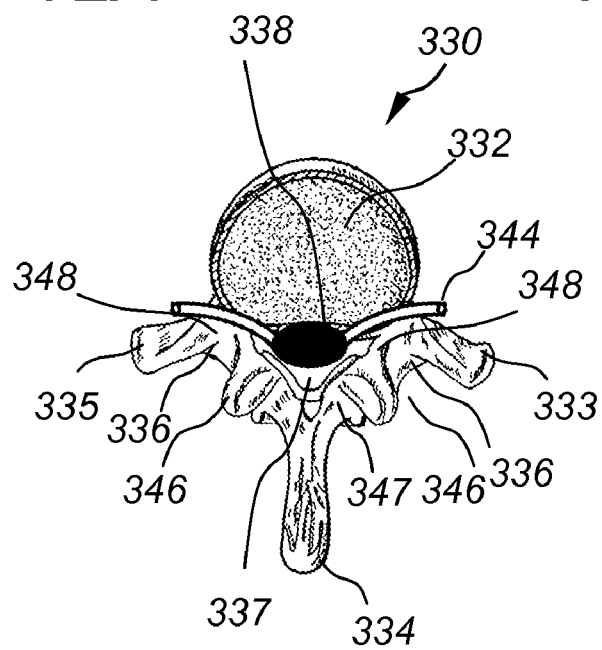
FIG. 12C

SPINOUS PROCESS FIXATION DEVICE

CROSS REFERENCE TO RELATED CO-PENDING APPLICATIONS

This application claims the benefit of U.S. provisional application Ser. No. 60/784,557 filed Mar. 21, 2006 and entitled "SPINOUS PROCESS FIXATION DEVICE", the contents of which are expressly incorporated herein by reference.

This application is also a continuation in part of U.S. application Ser. No. 11/609,418 filed on Dec. 12, 2006 and entitled SPINOUS PROCESS FIXATION IMPLANT, the contents of which are expressly incorporated herein by reference.

FIELD OF THE INVENTION

The present invention relates to a system and a method for spinal stabilization through an implant, and more particularly to spinal stabilization through attachment of the implant to the spinous processes along one or more vertebras.

BACKGROUND OF THE INVENTION

The human spine comprises individual vertebras 330 (segments) that are connected to each other to form a spinal column 329, shown in FIG. 12A. Referring to FIGS. 12B and 12C, each vertebra 330 has a cylindrical bony body (vertebral body) 332, three winglike projections (two transverse processes 333, 335 and one spinous process 334), left and right facet joints 346, lamina 347, left and right pedicles 348 and a bony arch (neural arch) 336. The bodies of the vertebrae 332 are stacked one on top of the other and form the strong but flexible spinal column. The neural arches 336 are positioned so that the space they enclose forms a tube, i.e., the spinal canal 337. The spinal canal 337 houses and protects the spinal cord and other neural elements. A fluid filled protective membrane, the dura 338, covers the contents of the spinal canal. The spinal column is flexible enough to allow the body to twist and bend, but sturdy enough to support and protect the spinal cord and the other neural elements. The vertebras 330 are separated and cushioned by thin pads of tough, resilient fiber known as inter-vertebral discs 340. Disorders of the spine occur when one or more of the individual vertebras 330 and/or the inter-vertebral discs 340 become abnormal either as a result of disease or injury. In these pathologic circumstances, fusion of adjacent vertebral segments may be tried to restore the function of the spine to normal, achieve stability, protect the neural structures, or to relief the patient of discomfort.

Several spinal fixation systems exist for stabilizing the spine so that bony fusion is achieved. The majority of these fixation systems utilize rods that attach to screws threaded into the vertebral bodies or the pedicles. In some cases plate fixation systems are also used to fuse two adjacent vertebral segments. This construction usually consists of two longitudinal plates that are each placed laterally to connect two adjacent pedicles of the segments to be fused. This system can be extended along the sides of the spine by connecting two adjacent pedicles at a time similar to the concept of a bicycle chain. Current plate fixation systems are basically designed to function in place of rods with the advantage of allowing intersegmental fixation without the need to contour a long rod across multiple segments. Both the plating systems and the rod systems add bulk along the lateral aspect of the spine limits access to the pars and transverse processes for decortication and placement of bone graft. In order to avoid this limitation many surgeons decorticate before placing the rods, thereby increasing the amount of blood loss and making it more difficult to maintain a clear operative field. Placing rods or plates lateral to the spine leaves the center of the spinal canal that contains the dura, spinal cords and nerves completely exposed. In situations where problems develop at the junction above or below the fused segments necessitating additional fusion, the rod fixation system is difficult to extend to higher or lower levels that need to be fused. Although there are connectors and techniques to lengthen the fixation, they tend to be difficult to use and time consuming.

Accordingly, there is a need for a spinal stabilization device that does not add bulk to the lateral aspect of the spine and does not limit access to the pars and transverse processes for decortication and placement of bone graft.

SUMMARY OF THE INVENTION

In general, in one aspect, the invention features an implantable assembly for stabilization of spinous processes, including a body, a bent arm and a straight arm. The body includes first and second crosspieces arranged parallel to each other, a first plate extending in a direction at right angle to first ends of the first and second crosspieces, first and second rings extending from second ends of the first and second crosspieces, respectively, and a second plate extending from a base of the first and second rings, at right angle to the first and second crosspieces and in an opposite direction to the first plate's direction. The second ends are arranged opposite to the first ends. The straight arm and bent arm are configured to pivot around an axis perpendicular to the first and second rings and to set first and second pivot angles with the first and second plates, respectively, thereby defining first and second spaces configured to receive first and second spinous processes, respectively.

Implementations of this aspect of the invention may include one or more of the following features. The straight arm extends along the first plate's direction and comprises a ring and a plate extending from a portion of the ring so that the plate's plane is perpendicular to the ring's plane. The straight arm plate comprises a first surface arranged opposite to a first surface of the first plate of the body. The bent arm comprises a bent shaft, a ring extending from a first end of the bent shaft and a plate extending form a second end of the bent shaft so that the plate's plane is perpendicular to the ring's plane. The bent arm plate comprises a first surface arranged opposite to a first surface of the second plate of the body. The straight arm ring and the bent arm ring are configured to be received within a gap formed between the first and second body rings. The assembly may further include a post member configured to pass through concentrically aligned through-bore openings formed in the first body ring, the straight arm ring, the bend arm ring and the second body ring. The post comprises outer threads configured to engage inner threads formed in the through-bore openings of the first body ring, the straight arm ring, the bend arm ring and the second body ring, consecutively, thereby locking and preventing the pivoting of the straight arm and the bent arm around the axis. The first surface of the first body plate, the first surface of the straight arm plate, the first surface of the second body plate and the first surface of the bent arm plate comprise protrusions configured to engage and frictionally lock the plates onto the first and second spinous processes positioned in the first space between the first body plate and the straight arm plate and the second space between the second body plate and the bent arm plate, respectively. The first and second crosspieces are dimensioned to fit between the first and second spinous processes and comprise edges sculpted to conform to the shape of the spinous processes. The first and second pivot angles comprise values between zero and 90 degrees. The assembly may be assembled prior to being implanted between the first and second spinous processes, or after being implanted between the first and second spinous processes. The assembly may further include a first locking member configured to lock the first plate's top end and the straight arm plate's top end to the first spinous process. The first locking member comprises a long bolt configured to be threaded through bolt holes formed through the first plate's top end, the first spinous process and the straight arm plate's top end and locks the first plate's top end, the first spinous process and the straight arm plate's top end by engaging a first nut after it exits the straight arm plate's bolt hole. The assembly may further include a second locking member configured to lock the second plate's bottom end and the bent arm plate's bottom end to the second spinous process. The second locking member comprises a long bolt configured to be threaded through bolt holes formed through the second plate's bottom end, the second spinous process and the bent arm plate's bottom end and locks the second plate's bottom end, the second spinous process and the bent arm plate's bottom end by engaging a second nut after it exits the bent arm plate's bolt hole. The first and second locking members may be staples, cables, sutures, pins or screws. The first and second plates, the straight arm and the bent arm may have adjustable lengths. The first and second crosspieces may have adjustable heights. The assembly may further include an extension body and the extension body may have first and second crosspieces arranged parallel to each other, a first plate extending in a direction at right angle to first ends of the first and second crosspieces, first and second rings extending from second ends of the first and second crosspieces, respectively, and a second plate extending at right angle to the first ends of the first and second crosspieces in an opposite direction to the first plate's direction. The second ends are arranged opposite to the first ends. The assembly may further include a second straight arm extending along the extension body second plate's direction and comprises a ring and a plate extending from a portion of the ring so that the plate's plane is perpendicular to the ring's plane. The second straight arm plate comprises a first surface arranged opposite to a first surface of the second plate of the extension body. The second straight arm is configured to pivot around an axis perpendicular to the extension body's first and second rings and to set a third pivot angle with the second plate of the extension body thereby defining a third space configured to receive a third spinous processes between the extension body's second plate and the second straight arm's first plate. The ring of the second straight arm is configured to be received within a gap formed between the extension body's first and second rings. The assembly may further include a second post member configured to pass through concentrically aligned through-bore openings formed in the extension body's first ring, the second straight arm ring and the extension body's second ring. The first surface of the extension body second plate, and the first surface of the second straight arm plate comprise protrusions configured to engage and frictionally lock the plates onto the third spinous process positioned in the third space between the extension body second plate and the straight arm plate. The extension body's first and second crosspieces are dimensioned to fit between the second and third spinous processes and comprise edges sculpted to conform to the shape of the spinous processes. The assembly may further include a third locking member configured to lock the extension body second plate's bottom end and the second straight arm plate's bottom end to the third spinous process. The third locking member comprises a long bolt configured to be threaded through bolt holes formed through the second straight arm plate's bottom end, the third spinous process and the extension body second plate's bottom end and locks the extension body second plate's bottom end and the second straight arm plate's bottom end to the third spinous process by engaging a third nut after it exits the second straight arm plate's bolt hole. The first plate of the extension body is attached to the second plate of the body. The first plate of the extension body is attached to the second plate of the body with the second locking member. The extension body first plate comprises a first surface having a spur configured to be received within a slot formed in the second plate of the body. The protrusions may teeth, spikes, serrations, rough coatings or ridges. The body, the extension body and the straight and bent arms may be made of stainless steel, titanium, gold, silver, alloys thereof, or absorbable material.

In general, in another aspect, the invention features a method for stabilizing spinous processes of a spinal column, including providing a body, a straight arm and a bent arm. The body comprises first and second crosspieces arranged parallel to each other, a first plate extending in a direction at right angle to first ends of the first and second crosspieces, first and second rings extending from second ends of the first and second crosspieces, respectively, wherein the second ends are arranged opposite to the first ends, and a second plate extending from a base of the first and second rings, at right angle to the first and second crosspieces and in an opposite direction to the first plate's direction. The method also includes engaging a first surface of the first plate with a first lateral surface of a first spinous process and a first surface of the second plate with a second lateral surface of a second spinous process. Next, engaging a first surface of the bent arm with a first lateral surface of the second spinous process and then engaging a first surface of the straight arm with a second lateral surface of the first spinous process. The bent arm and the straight arm are configured to pivot around an axis perpendicular to the first and second rings and to set first and second pivot angles with the first and second plates, respectively, thereby defining first and second spaces configured to receive the first and second spinous processes, respectively.

Among the advantages of this invention may be one or more of the following. The assembly stabilizes vertebras by attaching plates to the spinous processes of the vertebras. This stabilization device does not add bulk to the lateral aspect of the spine and does not limit access to the pars and transverse processes for decortication and placement of bone graft.

The details of one or more embodiments of the invention are set forth in the accompanying drawings and description below. Other features, objects and advantages of the invention will be apparent from the following description of the preferred embodiments, the drawings and from the claims

BRIEF DESCRIPTION OF THE DRAWINGS

Referring to the figures, wherein like numerals represent like parts throughout the several views. Various embodiments of the present invention will now be discussed with reference to the appended drawings. It is appreciated that these drawings depict only typical embodiments of the invention and are therefore not to be considered limiting of its scope.

FIG. 12A is a side view of the human spinal column;

FIG. 12B is an enlarged view of area A of FIG. 12A; and

FIG. 12C is an axial cross-sectional view of a lumbar vertebra.

DETAILED DESCRIPTION OF THE INVENTION

The present invention relates to a system and a method for a spinous process fixation implant.

Figure 1:
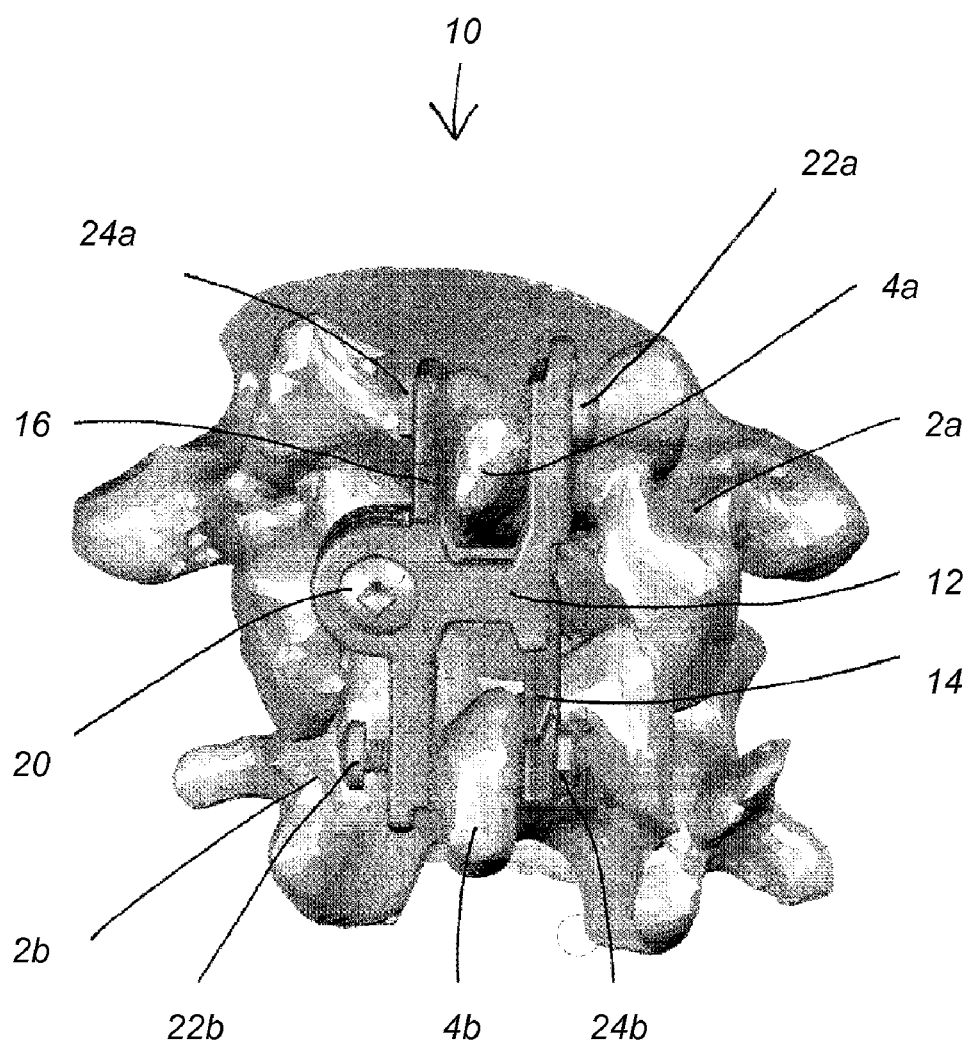
FIG. 1 is a posterior view of a portion of the spine with one embodiment of a spinous process fixation device of the present invention affixed thereto.

Referring to FIG. 1, a posterior view illustrates a portion of the spine with an embodiment of the present invention. A spinous process fixation device 10 includes a body 12, a bent arm 14, and a straight arm 16. A short bolt 20, two long bolts 22a, 22b, and nuts 24a, 24b hold the elements of the device 10 together. Each long bolt 22a, 22b also passes through one spinous process 4a, 4b securing the device 10 to the vertebrae 2a, 2b, respectively.

Figure 2:
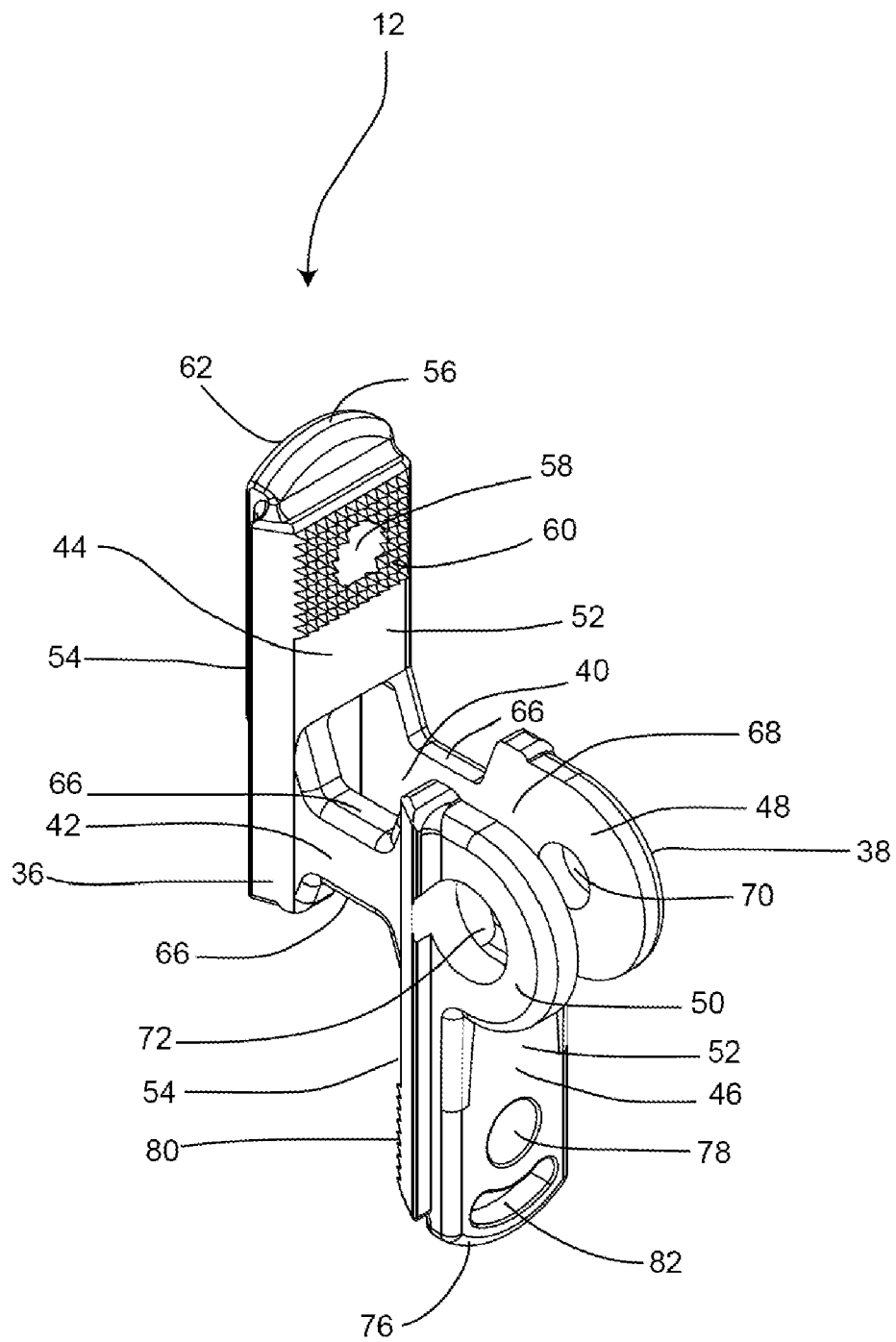
FIG. 2 is a perspective anterior view of the body of the device of FIG. 1.

FIGS. 2 through 8 display the device 10 in more detail. As seen in FIG. 2, the body 12 has an anterior side 36 and a posterior side 38. It includes a pair of crosspieces 40, 42. At a right angle to one end of the crosspieces 40, 42 is a first plate 44. At the opposite end of the crosspieces 40, 42, a pair of rings 48, 50 extends from the crosspieces. In the embodiment depicted in FIGS. 1 and 2 the rings are located at one end of the crosspieces, however in alternative embodiments they could be located at either end or in the center of the crosspieces, or anywhere on the body 12 which places them in the vicinity of or between the spinous processes when the device is implanted. A second plate 46 extends from the base of the rings 48, 50, at a right angle to the crosspieces 40, 42, and in the opposite direction from the first plate 44. Each crosspiece 40, 42 has edges 66 which are rounded and sculpted to correspond with the geometry of the spinous processes and lamina around which they will fit once implanted.

The first plate 44 is a substantially flat, rectangular surface extending perpendicularly from the crosspieces 40, 42. It has a first side 52 and a second side 54, and ends in a rounded terminus 56. A first bolt hole 58 passes through the first plate 44 near the terminus 56. Surrounding the bolt hole 58 on the first side 52 is a plurality of teeth 60 which protrude out of the surface of the first side. Indented into the second side 54, between the bolt hole 58 and the terminus 56, is a kidney-shaped first slot 62 (not visible in FIG. 2).

At the opposite end of the crosspieces 40, 42 from the first plate 44 are the rings 48, 50. The first ring 48 is a rounded extension of the first crosspiece 40, and the second ring 50 is a rounded extension of the second crosspiece 42. The rings 48, 50 are parallel to each other and a gap 68 between them is sized to hold portions of a straight arm 16 and a bent arm 14, as seen in FIG. 2. The first ring 48, which lies on the posterior side 38, has a circular first bore 70. This first bore 70 is sized to receive a short bolt 20. The second ring is on the anterior side 36, and has a circular second bore 72. This second bore 72 is larger in diameter than the first bore 70, and is sized to receive a short bolt 20 plus a portion of the straight arm 16.

The second plate 46 extends at a right angle from the rings 48, 50 and ends in a rounded terminus 76. A second bolt hole 78 penetrates the plate 46 near the terminus 76. On the first side 52, in between the terminus 76 and the bolt hole 78 is a kidney-shaped second slot 82. On the second side 54, surrounding the second bolt hole 78 is a plurality of teeth 80.

Figure 3:
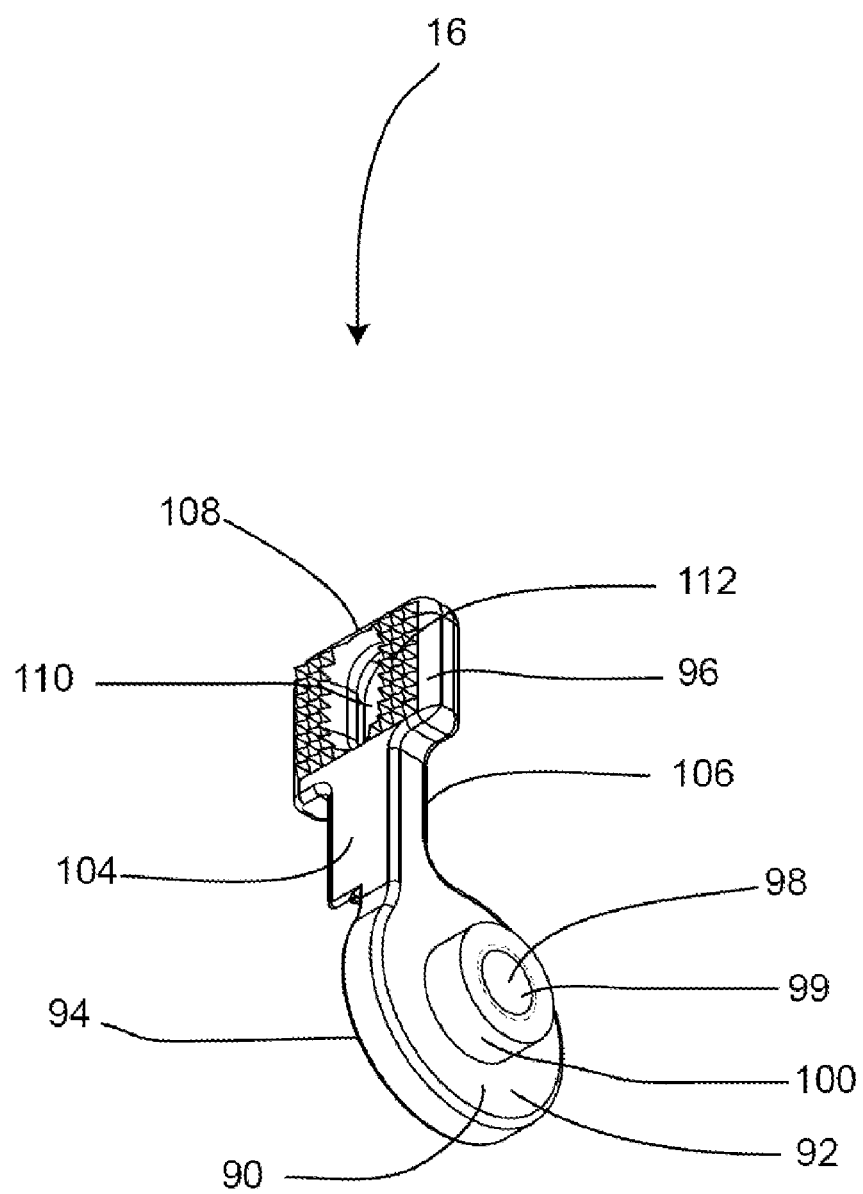
FIG. 3 is a perspective anterior view of the straight arm of the device of FIG. 1.
Figure 4:
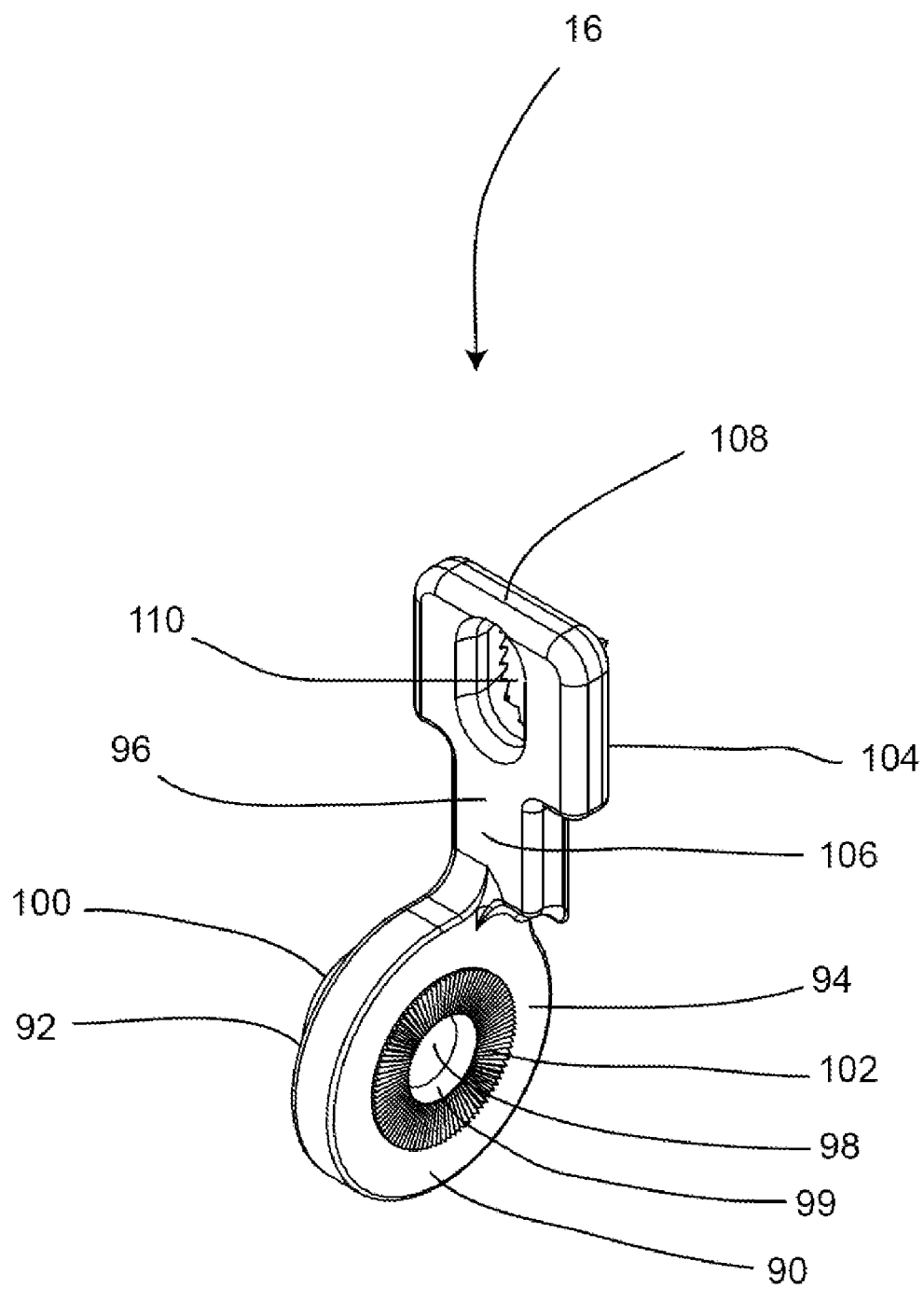
FIG. 4 is a perspective posterior view of the straight arm of FIG. 3.

As seen in FIGS. 1 and 2, the rings 48, 50 form the pivot point for the body 12. A pivotable straight arm 16 fits in the gap 68 between the rings 48, 50 of the body 12, and extends in the same direction as the first plate 44. FIGS. 3 and 4 display the straight arm 16 in more detail. One end of the straight arm 16 is a ring 90, and extending from a portion of the ring is a plate 96, which forms the remainder of the straight arm. The ring 90 has an anterior side 92 and a posterior side 94. In the center of the ring 90 is a bore 98, sized to fit the short bolt 20. A protruding annulus 100 surrounds the bore 98 and projects outward from the anterior side 92. The bore 98, through both the ring 90 and the annulus 100, is encircled by a threaded wall 99 (threads not visible in FIGS. 3 and 4). Surrounding the bore 98 on the posterior side 94 of the ring 90 is a radial spline 102.

The plate 96 extends away from the ring 90 such that the plane of the plate is perpendicular to the plane of the ring. The plate has a first side 104, a second side 106, and ends in a terminus 108. Adjacent to the terminus 108 is a bolt hole 110, which is has a diameter to fit a long bolt 22, but is elongated to allow the vertical placement of the arm 16 on the bolt 22 to be adjustable. A plurality of teeth 112 surround the bolt hole 110, projecting outward from the first side 104.

Figure 5:
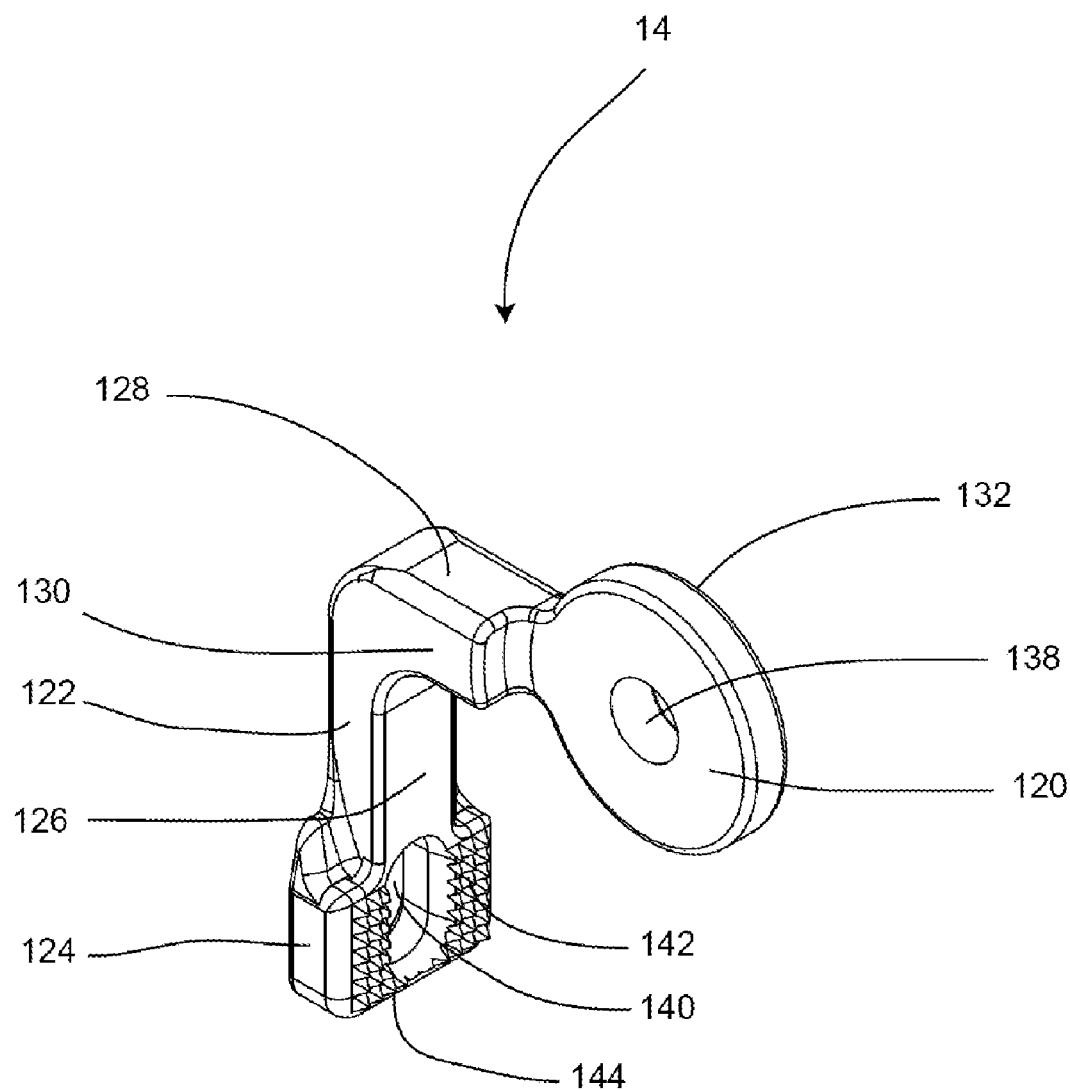
FIG. 5 is a perspective anterior view of the bent arm of the device of FIG. 1.
Figure 6:
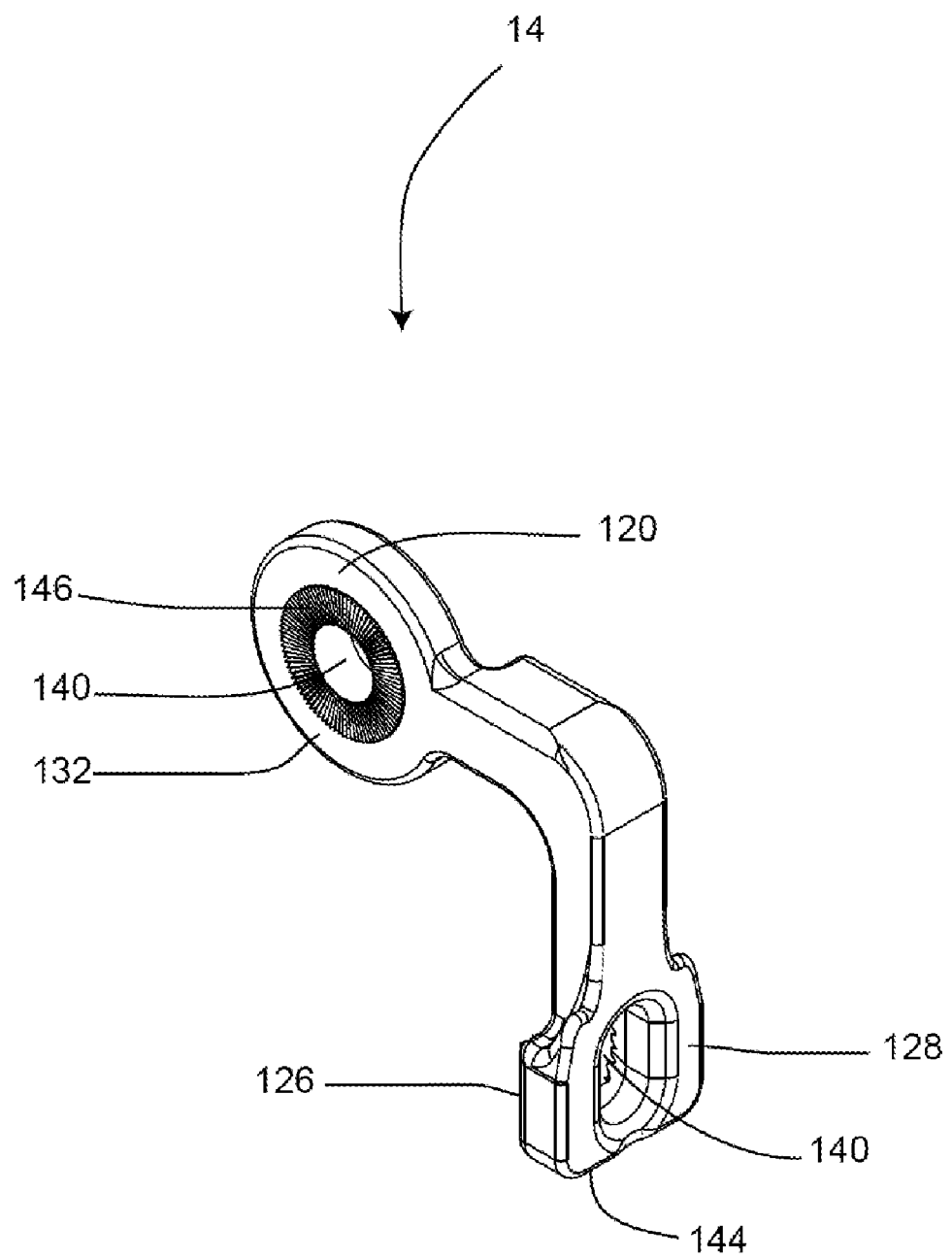
FIG. 6 is a perspective posterior view of the bent arm of FIG. 5.

Returning briefly to FIGS. 1 and 2, a bent arm 14 also fits in the gap 68 between the rings 48, 50 of the body 12. FIGS. 5 and 6 show the bent arm 14 in more detail. The bent arm 14 is comprised of a bent shaft 122, a ring 120 and a plate 124. The shaft 122 is an elongated member which is bent at a right angle near its center. The shaft 122 has a first side 126 on the inside of the bend; a second side 128 is on the outside; and anterior 130 and posterior 132 sides. One end of the bent shaft 122 connects to a ring 120, and the opposite end terminates in a plate 124. The ring 120 also has an anterior side 130 which is a continuation of the anterior side of the shaft 122, and a posterior side 132 which is a continuation of the posterior side of the shaft 122. In the center of the ring 120 is a circular bore 138, whose diameter is sized to fit a short bolt 20. On the posterior side 132 of the ring 120, a radial spline 146 surrounds the bore 138.

At the opposite end of the shaft 122 from the ring 120 is the plate 124. The plate 124 is generally rectangular, and has a first side 126 which is a continuation of the first side of the shaft 122. A second side 128 is a continuation of the second side of the shaft 122. The plate 124 ends in a terminus 144. Passing through the first and second sides 126, 128 adjacent to the terminus 144 is a bolt hole 140. The bolt hole 140 has a diameter to fit a long bolt 22 but is elongated along the long axis of the shaft 122 so the placement of the bent arm 14 can be adjustable relative to the bolt 22. Surrounding the bolt hole 140 and projecting from the first side 126 is a plurality of teeth 142.

Figure 7:
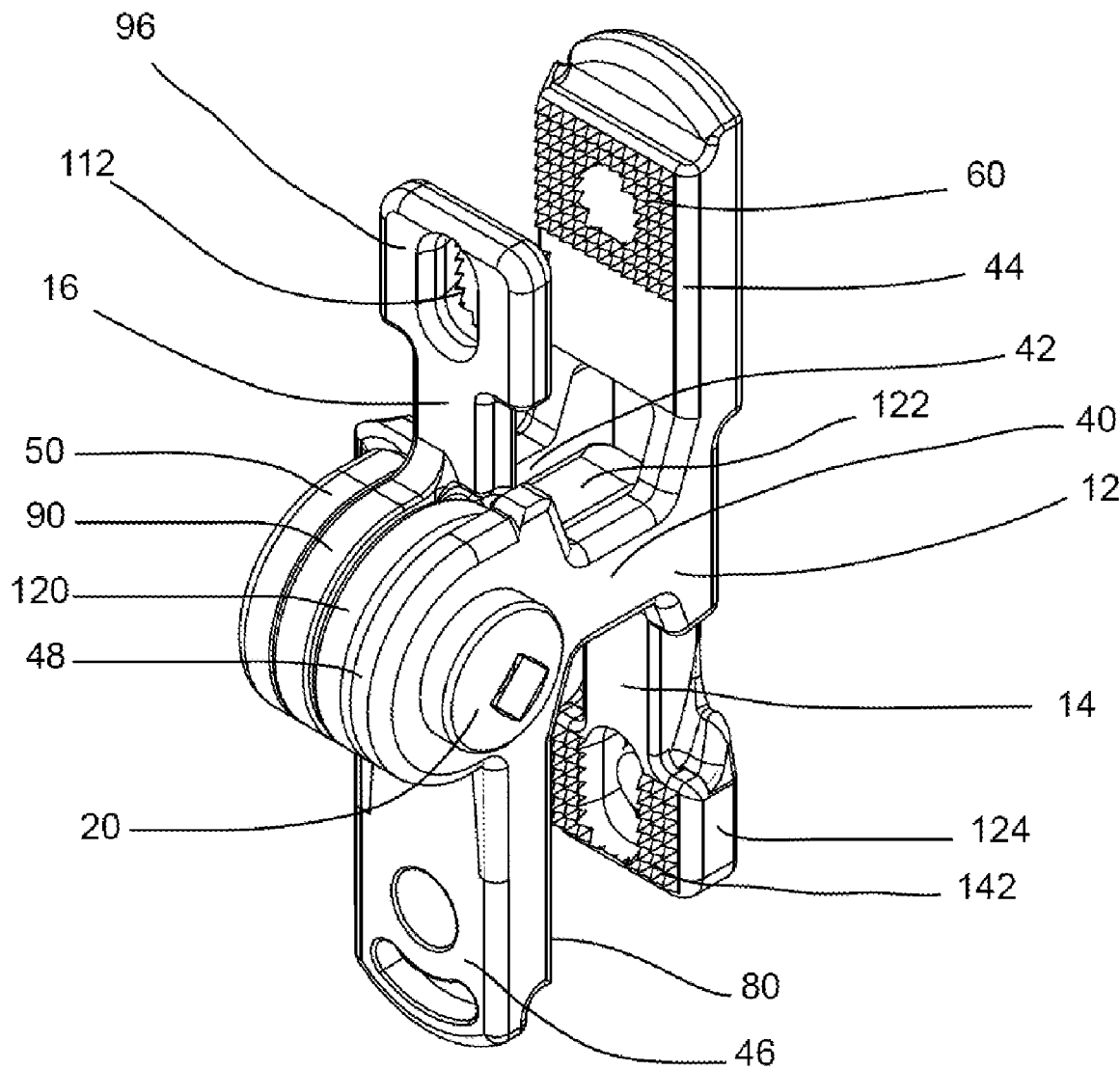
FIG. 7 is a perspective posterior view of the body of FIG. 2 with the straight arm of FIG. 3 and the bent arm of FIG. 5 attached.

As shown in FIG. 7, a body 12, bent arm 14, and straight arm 16 are assembled to form one embodiment of the spinous process fixation device. The ring 90 of the straight arm 16 is placed between the rings 48, 50 of the body 12, and the protruding annulus 100 is fitted into the larger second bore 72 on the second ring 50. The plate 96 of the straight arm 16 is positioned so it is approximately parallel to the first plate 44 of the body 12. Next, the ring 90 of the bent arm 14 is slid in between the first ring 48 of the body 12 and the ring 90 of the straight arm 16. The shaft 122 of the bent arm 14 fits between the crosspieces 40, 42 of the body 12. The bent arm 14 is positioned so that its plate 124 is approximately parallel to the second plate 46 of the body 12.

Figure 8:
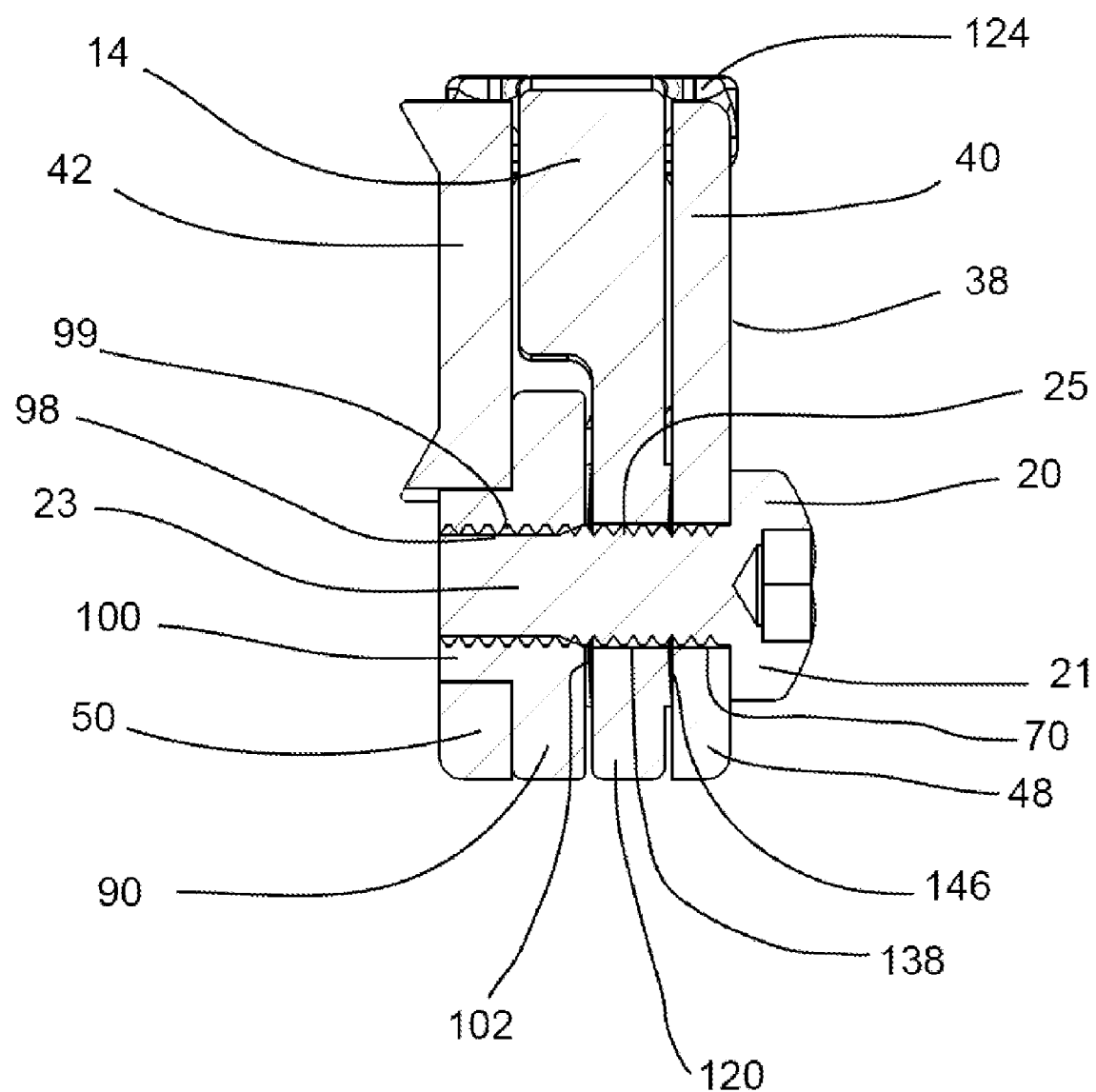
FIG. 8 is a cross-sectional view of the assembly of FIG. 7 as seen from a caudal perspective.

With all pieces 12, 14, 16 assembled thus, a short bolt 20 is slid into place from the posterior side 38 of the body 12. FIG. 8 shows a cross-sectional view of the bolt 20 where it intersects the body ring 48, the bent arm ring 120, and the straight arm ring 90. The bolt 20 has a head 21, and a shaft 23 which is encircled by threads 25. The bolt 20 passes through the first bore 70 (of the body 12), through the bore 138 (of the bent arm 14), and finally to the bore 98 (of the straight arm 16). When the bolt 20 reaches the bore 98, threads 25 on the shaft 23 engage with the threaded wall 99 of the bore 98. The bolt 20 is turned until the head 21 meets the posterior ring 48 (of the body 12). As the bolt 20 is turned further, the engagement of the threads pulls the straight arm ring 90 posteriorly, tightening the straight arm ring 90, the bent arm ring 120, and the body ring 48 together. As the rings are tightened, the radial spline 102 on the straight arm 16 is pressed against the anterior side of the bent arm's ring 120. Similarly, the radial spline 146 on the bent arm 14 is pressed against the anterior side of the body's posterior ring 48.

The assembled components are implanted into the patient with the use of instrumentation (not shown) between two adjacent spinous processes 4a, 4b, as seen in FIGS. 1 and 7. The crosspieces 40, 42 are placed between the spinous processes 4a, 4b, so that the plates 44, 46, 96, 124 fall on the lateral sides of the spinous processes. One spinous process 4a lies between the first plate 44 (of the body) and the plate 96 (of the straight arm), and the other spinous process 4b lies between the second plate 46 and the plate 124 (of the bent arm). On each of the plates 44, 46, 96, 124, the corresponding teeth 60, 80, 112, 142 face toward the lateral surface of the adjacent spinous process. At this point, the arms 14, 16 are pivoted as necessary to provide the desired fit of the plates to the spinous processes. The bolt 20 is tightened, clamping the teeth 60, 80, 112, 142 into the surfaces of the spinous processes. The radial splines 102, 146 are pressed into their adjacent surfaces. The protruding teeth and splines create additional friction which helps prevent the device from shifting or slipping.

Long bolts 22a, 22b may be added to this embodiment to further anchor the device on the spinous processes 4a, 4b, respectively. If they are added, appropriately sized holes must be drilled laterally through the spinous processes prior to placement of the device. Once the device is in place as described above, one long bolt 22a is threaded through the bolt hole 58 on the first plate 44 of the body 12, through the drilled hole in the spinous process 4a, then out through the bolt hole 110 on the straight arm 16. The second long bolt 22b is threaded through the bolt hole 78 on the second plate 46, through the drilled hole in the spinous process 4b, then out through the bolt hole 140 on the bent arm 14. The fit of the device may be adjusted by loosening the short bolt 20 and pivoting the arms 14, 16 until the proper orientation is found. The elongated bolt holes 110, 140 on the arms allow for adjustment of the arms 14, 16 while still being able to receive the ends of the long bolts 22a, 22b. The short bolt 20 is tightened, and nuts 24a, 24b are screwed on the ends of the long bolts 22a, 22b, respectively, and tightened.

In this embodiment of the invention, a plurality of bolts and nuts holds the elements of the device 10 together and secures them to the vertebrae. The use of bolts adds adjunctive tension to the plates, and adds additional strength during flexion and extension. However, pins, screws, cables, or other connecting elements may be implemented instead to connect and secure the elements of the device.

The primary indication of the device 10 is as an adjunctive fixation device, in association with an interbody fusion device. However, if desired, the device as described may also be use as a dynamic stabilization device, if the plates are not clamped down tightly on the spinous processes. The device 10 may also be used as described as an X stop, reducing pressure on the intervertebral disks during extension.

When the device 10 is used as an adjunctive fixation device, it may be desirable to add bone ingrowth surfaces to the edges 66 of the crosspieces 40, 42. The bone ingrowth surfaces may be additive, such as but not restricted to plasma spray, laser deposition of metal, or a sintered bead coating. Alternatively, the bone ingrowth surfaces may be created by electrochemical etching or other removal processes. If the device is to be used as a dynamic stabilization device or an X stop, no bone ingrowth surfaces would be created.

Figure 9:
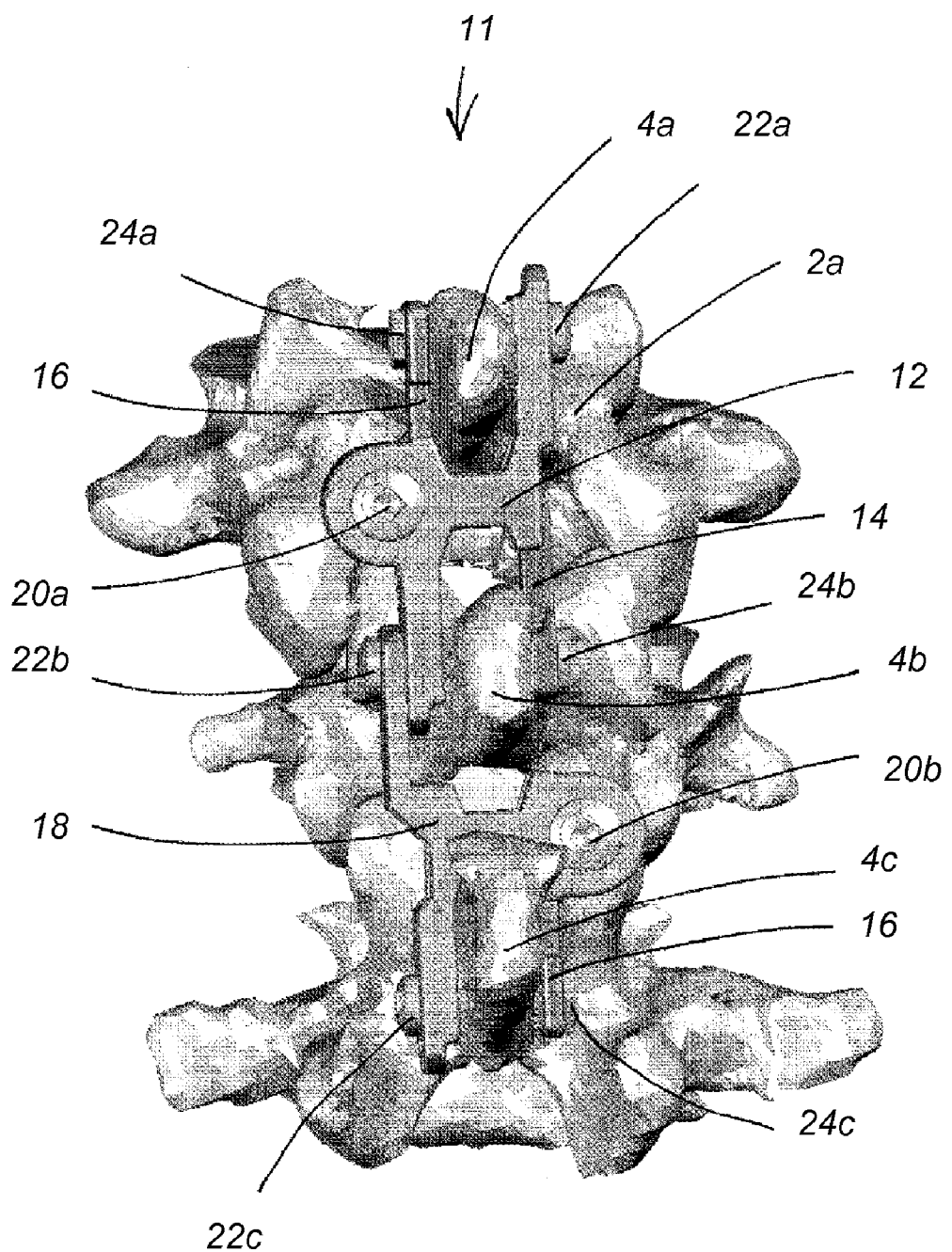
FIG. 9 is a posterior view of a portion of the spine with a spinous process fixation device according to an alternative embodiment of the present invention affixed thereto.

An alternative embodiment of the device is depicted in FIG. 9, bolted through three spinous processes 4a, 4b, 4c. This device is indicated when more than two adjacent spinous processes require fixation. The device 11 includes a body 12, a bent arm 14, two straight arms 16, an extension body 18, and a plurality of bolts 20a, 20b, 22a, 22b, 22c and nuts 24a-24c. The embodiment shown in FIG. 9 has one body 12 and one extension body 18; another embodiment could include one body 12 with two extension bodies 18, one added on either end of the body 12. Yet other embodiments could include one body 12 with one extension body 18 linked to it, and one or more extension bodies 18 linked to the first extension body 18 in succession, depending on how many spinous processes are to be fixed.

Figure 10:
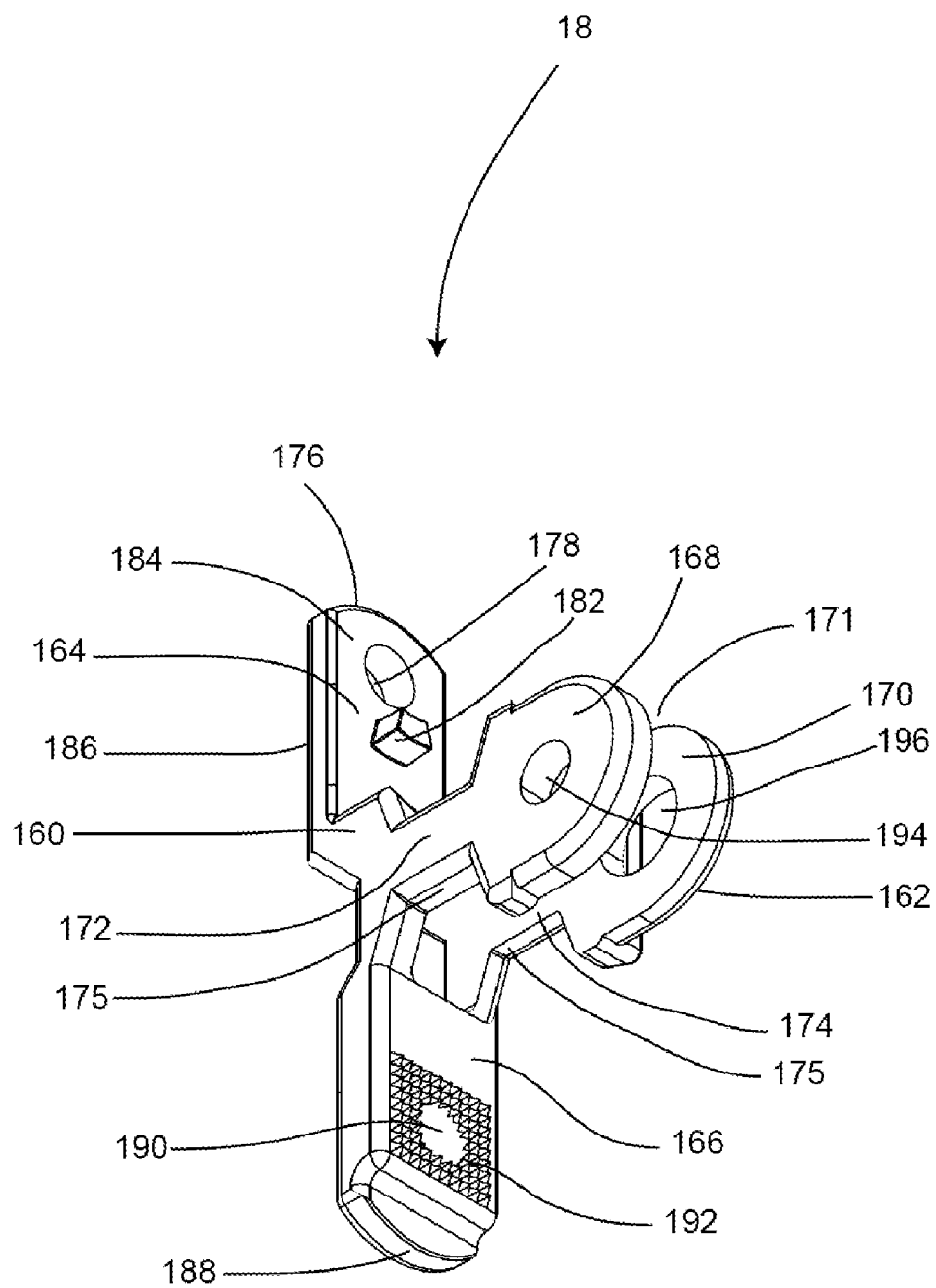
FIG. 10 is a perspective posterior view of the extension body of FIG. 9.

FIG. 10 shows the extension body 18 in greater detail. The extension body 18 has a posterior side 160 and an anterior side 162. A first plate 164 occupies one end of the body, and a second plate 166 is at the opposite end. A posterior ring 168 and an anterior ring 170 lie perpendicular to the plates 164, 166, with a gap 171 between them. A posterior crosspiece 172 connects the posterior ring 168 to the posterior edges of the plates 164, 166, and an anterior crosspiece 174 connects the anterior ring 170 to the anterior edges of the plates 164, 166. Each crosspiece 172, 174 has edges 175 which are rounded and sculpted to correspond with the geometry of the spinous processes and lamina around which they will fit once implanted. As with the body 12, bone ingrowth surfaces may be created on the edges 175 if the device 11 is to be used as an adjunctive fixation device.

The first plate 164 is generally flat and rectangular, and one rectangular end terminates in a rounded terminus 176. The plate 164 has a flat first side 184 and a flat second side 186. Adjacent to the terminus 176 and passing through both sides 184, 186 is a bolt hole 178. A spur 182 projects from the first side 184, on the opposite side of the bolt hole 178 from the terminus 176.

The second plate 166 extends in the opposite direction but on the same plane as the first plate 164. The second plate 166 is also generally flat and rectangular, and ends in a rounded terminus 188. Adjacent to the terminus 188, a bolt hole 190 is open from the first side 184 to the second side 186. Surrounding the bolt hole 190 are a plurality of teeth 192 which project outward from the first side 184.

The rings 168, 170 are parallel to one another and are perpendicular to the plates 164, 166, extending in the direction of the first side 164. The posterior ring 168 has a central first bore 194 which is sized to fit the diameter of a short bolt 20b. The anterior ring 170 has a central second bore 196 which is wider in diameter, sized to fit the annulus 100 on a straight arm 16 (as seen in FIG. 4).

Figure 11:
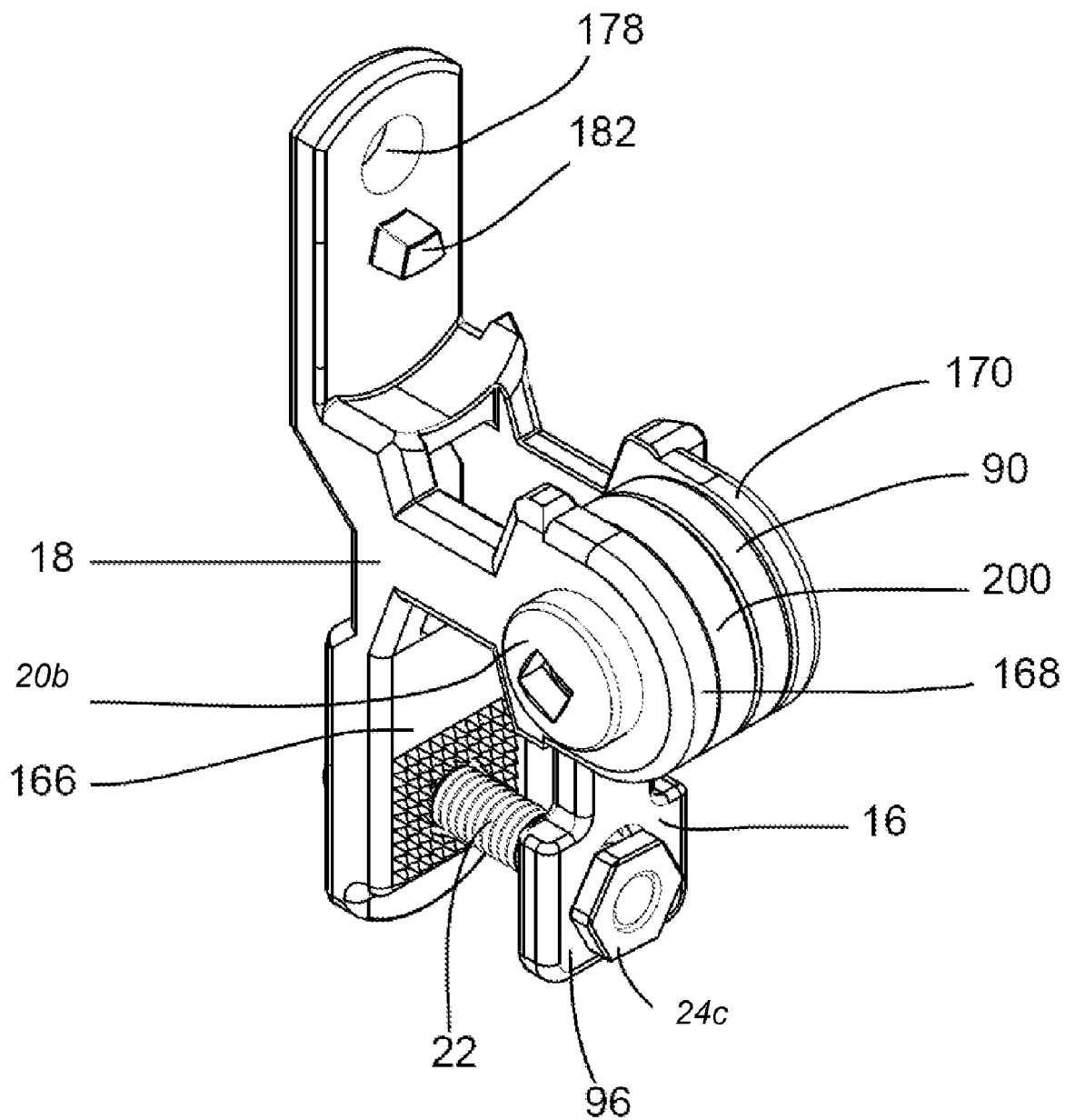
FIG. 11 is a perspective view of the extension body of FIG. 9 with the straight arm of FIG. 3 attached.

An extension body 18 linked to a straight arm 16 is depicted in FIG. 11. The straight arm, as seen also in FIGS. 3 and 4, has a ring 90 and a plate 96. The ring 90 is put into the gap 171 between the rings 168, 170 of the extension body 18. The annulus 100 on the ring 90 fits into the second bore 196 on the anterior ring 170. A circular washer 200 fits into the remainder of the gap 171, between the ring 90 and the posterior ring 168. A short bolt 20b is inserted from the posterior side 160 through the bore 194, the washer 200, and the bores 98, 196. The straight arm 16 is pivoted on the bolt 20b so its plate 96 is approximately parallel to the plate 166 on the extension body 18.

In this embodiment of the invention, the rings 168, 170 are located at one end of the crosspieces 172, 174. The rings 168, 170 and their associated short bolt 20 form a pivot point for adjusting the fit of the plates 96, 166 around the spinous process. In alternative embodiments of the invention, the rings and therefore the pivot point could be located at the center of the crosspieces, at the other end of the crosspieces, or any other location on the extension body which puts the pivot point in the vicinity of or between the spinous process.

Referring to FIGS. 7, 9 and 11, the extension body 18 with the attached straight arm 16 is connected to the body 12 by lining up the first plate 164 of the extension body 18 with the second plate 46 of the body 12. The first side 184 of the extension body 18 is placed against the first side 52 of the body 12, so that the bolt holes 78, 178 line up. The spur 182 on the extension body 18 fits into the slot 82 on the body 12. A long bolt 22b is passed from the second side 186 of the extension body and through both bolt holes 78, 178. It then passes through the hole in the spinous process 4b and through the bolt hole 140 on the bent arm 14.

Several adjustments may be made to fit the device to the spinous processes. The longitudinal angle of the extension body 18 relative to the body 12 is adjusted by pivoting the extension body 18 around the long bolt 22b. The spur 182 slides within the slot 82, allowing for some adjustment but preventing slippage beyond a certain point. Once the correct angle is found, a nut 24b is added to the end of the bolt 22b and tightened.

After the angle adjustment is made to the extension body 18, the final long bolt 22c connects the second plate 166 to the straight arm 16. It is threaded from the second side 186 of the extension body 18 through the bolt hole 190, through the hole in the spinous process 4c, then through the bolt hole 110 on the straight arm 16.

The angle of the straight arm 16 attached to the extension body 18 is adjusted by pivoting it around the short bolt 20b. The elongated shape of the bolt hole 110 allows for some movement of the straight arm 16 while still allowing the long bolt 22c to reach through the hole 110. Once the correct fit is found, the short bolt 20b is tightened. As it is tightened, the radial spline 102 on the straight arm 16 is pressed into the washer 200, creating additional friction. A nut 24c is added to the end of the long bolt 22c and tightened. As the nut 24c is tightened, the plates 96, 166 and their teeth 112, 192 are pressed in and grip the spinous process 4c.

The fit of the spinous fixation device on the spinous processes is determined by two factors: the size of the component pieces and their ability to be pivoted. The body, extension body, straight arm and bent arm components are all available in small, medium and large sizes. All three sizes are of a standard depth (posterior to anterior direction) but increase in length from small to large. The lateral width of the device is determined by the pivotability of the components around the short bolts. The elongated bolt holes on the ends of the straight and bent arms allow those pieces freedom to be pivoted laterally yet still be connectable to the long bolts.

The device is conformed to the lordotic or kyphotic angle of the spine by the pivotability of the components around the long bolts. The plates of the body and the extension body (or bodies, if three or more spinous processes are fixed) are swiveled posteriorly or anteriorly at infinite increments to fit the spine prior to the tightening of the long bolt. The spur and slot mechanism which engages when an extension body is linked to a body allows for several degrees of rotation but prevents slipping.

The present invention may be embodied in other specific forms without departing from its spirit or essential characteristics. As such, the described embodiments are to be considered in all respects only as illustrative and not restrictive. Other embodiments are within the scope of the following claims. For example, vertebras 2a and 2b may be any two vertebras, including lumbar L1-L5, thoracic T1-T12, cervical C1-C7 or the sacrum. The fixation assembly 10 may extend along multiple vertebras. The body structure 12 may be also configured as a mirror image of the structure in FIG. 1, with the pivoting straight arm 16 located on the right side of spinous process 4a and bend arm 14 located on the left side spinous process 4b of the FIG. 1. Plates 44, 46 96, 124 may have adjustable lengths. Crosspieces 40, 42 may have adjustable heights.

Several embodiments of the present invention have been described. Nevertheless, it will be understood that various modifications may be made without departing from the spirit and scope of the invention. Accordingly, other embodiments are within the scope of the following claims.

What is claimed is:

1. An implantable assembly for stabilization of spinous processes, comprising:
   a body comprising first and second crosspieces arranged parallel to each other, a first plate extending in a direction at right angle to first ends of said first and second crosspieces, first and second rings extending from second ends of said first and second crosspieces, respectively, wherein said second ends are arranged opposite to said first ends, and a second plate extending from a base of said first and second rings, at right angle to said first and second crosspieces and in an opposite direction to said first plate's direction;
   a bent arm;
   a straight arm; and
   wherein said straight arm and said bent arm are configured to pivot around an axis perpendicular to said first and second rings and to set first and second adjustable pivot angles with said first and second plates, respectively, thereby defining first and second spaces configured to receive first and second spinous processes, respectively.

2. The assembly of claim 1 wherein said straight arm extends along said first plate's direction and comprises a ring and a plate extending from a portion of said ring so that said plate's plane is perpendicular to said ring's plane and wherein said plate comprises a first surface arranged opposite to a first surface of said first plate of said body.

3. The assembly of claim 2 wherein said bent arm comprises a bent shaft, a ring extending from a first end of said bent shaft and a plate extending form a second end of said bent shaft so that said plate's plane is perpendicular to said ring's plane and wherein said plate comprises a first surface arranged opposite to a first surface of said second plate of said body.

4. The assembly of claim 3 wherein said straight arm ring and said bent arm ring are configured to be received within a gap formed between said first and second body rings.

5. The assembly of claim 4 further comprising a post member configured to pass through concentrically aligned through-bore openings formed in said first body ring, said straight arm ring, said bend arm ring and said second body ring.

6. The assembly of claim 5 wherein said post comprises outer threads configured to engage inner threads formed in said through-bore openings of said first body ring, said straight arm ring, said bend arm ring and said second body ring, consecutively, thereby locking and preventing said pivoting of said straight arm and said bent arm around said axis.

7. The assembly of claim 6 wherein said first surface of said first body plate, said first surface of said straight arm plate, said first surface of said second body plate and said first surface of said bent arm plate comprise protrusions configured to engage and frictionally lock said plates onto said first and second spinous processes positioned in said first space between said first body plate and said straight arm plate and said second space between said second body plate and said bent arm plate, respectively.

8. The assembly of claim 7 wherein said first and second crosspieces are dimensioned to fit between said first and second spinous processes and comprise edges sculpted to conform to the shape of said spinous processes.

9. The assembly of claim 8 further comprising a first locking member configured to lock said first plate's top end and said straight arm plate's top end to said first spinous process.

10. The assembly of claim 9 wherein said first locking member comprises a long bolt configured to be threaded through bolt holes formed through said first plate's top end, said first spinous process and said straight arm plate's top end and locks said first plate's top end, said first spinous process and said straight arm plate's top end by engaging a first nut after it exits said straight arm plate's bolt hole.

11. The assembly of claim 9 further comprising a second locking member configured to lock said second plate's bottom end and said bent arm plate's bottom end to said second spinous process.

12. The assembly of claim 11 wherein said second locking member comprises a long bolt configured to be threaded through bolt holes formed through said second plate's bottom end, said second spinous process and said bent arm plate's bottom end and locks said second plate's bottom end, said second spinous process and said bent arm plate's bottom end by engaging a second nut after it exits said bent arm plate's bolt hole.

13. The assembly of claim 12 further comprising an extension body, said extension body comprising first and second crosspieces arranged parallel to each other, a first plate extending in a direction at right angle to first ends of said first and second crosspieces, first and second rings extending from second ends of said first and second crosspieces, respectively, wherein said second ends are arranged opposite to said first ends, and a second plate extending at right angle to said first ends of said first and second crosspieces in an opposite direction to said first plate's direction.

14. The assembly of claim 13 further comprising a second straight arm extending along said extension body second plate's direction and comprises a ring and a plate extending from a portion of said ring so that said plate's plane is perpendicular to said ring's plane and wherein said plate comprises a first surface arranged opposite to a first surface of said second plate of said extension body.

15. The assembly of claim 14 wherein said second straight arm is configured to pivot around an axis perpendicular to said extension body's first and second rings and to set a third pivot angle with said second plate of said extension body thereby defining a third space configured to receive a third spinous processes between said extension body's second plate and said second straight arm's first plate.

16. The assembly of claim 15 wherein said ring of said second straight arm is configured to be received within a gap formed between said extension body's first and second rings.

17. The assembly of claim 16 further comprising a second post member configured to pass through concentrically aligned through-bore openings formed in said extension body's first ring, said second straight arm ring and said extension body's second ring.

18. The assembly of claim 17 wherein said first surface of said extension body second plate, and said first surface of said second straight arm plate comprise protrusions configured to engage and frictionally lock said plates onto said third spinous process positioned in said third space between said extension body second plate and said straight arm plate.

19. The assembly of claim 18 wherein said extension body's first and second crosspieces are dimensioned to fit between said second and third spinous processes and comprise edges sculpted to conform to the shape of said spinous processes.

20. The assembly of claim 19 further comprising a third locking member configured to lock said extension body second plate's bottom end and said second straight arm plate's bottom end to said third spinous process.

21. The assembly of claim 20 wherein said third locking member comprises a long bolt configured to be threaded through bolt holes formed through said second straight arm plate's bottom end, said third spinous process and said extension body second plate's bottom end and locks said extension body second plate's bottom end and said second straight arm plate's bottom end to said third spinous process by engaging a third nut after it exits said second straight arm plate's bolt hole.

22. The assembly of claim 15 wherein said first plate of said extension body is attached to said second plate of said body.

23. The assembly of claim 22 wherein said first plate of said extension body is attached to said second plate of said body with said second locking member.

24. The assembly of claim 23 wherein said extension body first plate comprises a first surface having a spur configured to be received within a slot formed in the second plate of said body.

25. The assembly of claim 11 wherein said first and second locking members are selected from a group consisting of staples, cables, sutures, pins and screws.

26. The assembly of claim 7 wherein said protrusions are selected from a group consisting of teeth, spikes, serrations, rough coatings and ridges.

27. The assembly of claim 26 wherein said body, and said straight and bent arms comprise materials selected from a group consisting of stainless steel, titanium, gold, silver, alloys thereof, and absorbable material.

28. The assembly of claim 1, wherein said first and second pivot angles comprise values between zero and 90 degrees.

29. The assembly of claim 1 wherein said assembly is assembled prior to being implanted between said first and second spinous processes.

30. The assembly of claim 1 wherein said assembly is assembled after being implanted between said first and second spinous processes.

31. The assembly of claim 1 wherein said first and second plates, said straight arm and said bent arm comprise adjustable lengths.

32. The assembly of claim 1 wherein said first and second crosspieces comprise adjustable heights.

* * * * *